United States Patent [19]

Wink et al.

[11] Patent Number: 5,260,491
[45] Date of Patent: Nov. 9, 1993

[54] CATIONIC RHODIUM BIS(DIOXAPHOSPHORUS HETEROCYCLE) COMPLEXES AND THEIR USE IN THE BRANCHED PRODUCT REGIOSELECTIVE HYDROFORMYLATION OF OLEFINS

[75] Inventors: Donald J. Wink, New York; Thomas J. Kwok, Bethpage, both of N.Y.

[73] Assignee: New York University, New York, N.Y.

[21] Appl. No.: 966,841

[22] Filed: Oct. 27, 1992

Related U.S. Application Data

[62] Division of Ser. No. 587,186, Sep. 24, 1990, Pat. No. 5,179,055.

[51] Int. Cl.$^5$ ............................................. C07C 45/50
[52] U.S. Cl. .................................. 568/454; 568/451; 502/166
[58] Field of Search ..................... 568/451, 452, 454

[56] References Cited

U.S. PATENT DOCUMENTS

| | | | |
|---|---|---|---|
| 4,268,688 | 5/1981 | Tinker et al. | 568/454 |
| 4,668,651 | 5/1987 | Billig | 568/454 |
| 4,769,498 | 9/1988 | Billig | 568/454 |

FOREIGN PATENT DOCUMENTS

| | | | |
|---|---|---|---|
| 48-099131 | 12/1973 | Japan | 568/454 |
| 52-062233 | 5/1977 | Japan | 568/454 |
| 54-021843 | 2/1979 | Japan | 568/454 |
| 58-035140 | 3/1983 | Japan | 568/454 |
| 63-233945 | 9/1988 | Japan | 568/454 |
| 63-290837 | 11/1988 | Japan | 568/454 |
| 01013047 | 1/1989 | Japan | 568/454 |
| 01029335 | 1/1989 | Japan | 568/454 |
| 2217318 | 10/1989 | United Kingdom . | |

OTHER PUBLICATIONS

Organometallic (1988), 7, 33–37 (Bleek et al).
Lai et al., "Substituent Effects in the Cobalt and Rhodium Catalyzed Hydroformylation of Ring Substituted Styrenes", *J. Mol. Catalysis* 4:401–410 (1978).
Hayashi, T. et al., "Hydroformylation of p-Substituted Styrenes Catalyzed by Rhodium-Triphenylphosphine Complexes", *J. Mol. Catalysis* 13:323–330 (1981).

(List continued on next page.)

*Primary Examiner*—Werren B. Lone
*Attorney, Agent, or Firm*—Browdy and Neimark

[57] ABSTRACT

Cationic rhodium bis(dioxaphosphorus heterocycle) complexes of the formula:

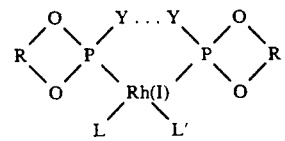

in which R is preferably

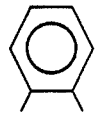

or $(CH_2)_{2-5}$, Y...Y is any backbone chain of 2–5 atoms, and L and L' are any stabilizing ligands, used in hydroformylation of olefins to obtain regioselectivity of branched aldehyde products. The formula of the catalyst may include substituents which do not interfere with the branched product regioselectivity of the catalyst as a whole. In the hydroformylation method the olefin is reacted with hydrogen and carbon monoxide in the presence of the catalyst at a temperature and pressure sufficient to permit the desired branched product regioselectivity.

22 Claims, No Drawings

OTHER PUBLICATIONS

Lazzaroni, R. et al., "Regioselectivity in the Rhodium-Catalyzed Hydroformylation of Styrene as a function of Reaction Temperature and Gas Pressure", *J. Mol. Catalysis* 50:1–9 (1989).

Neibecker, D. et al., "Synthesis of 2-Arylpropionaldehydes through Hydroformylation", *J. Org. Chem.* 54:5208–5210 (1989).

Amer, I. et al., "Zwitterionic Rhodium Complexes as Catalysts for the Hydroformulation of Olefins", *J. Am. Chem. Soc.* 112:3674–3676 (1990).

Brown, J. et al., "Hydroformylation Catalyzed by Rhodium Complexes of Trehalose-Derived Ligands aa and ββ Tredip; a Highly Regioselective Route to α-Methylarylpropionaldehydes"; *Tetrahedron* 42(18):5105 (1986).

Tanaka, M. et al., "Asymmetric Hydroformylation of Styrene. The Effects of the Reaction Conditions on the Stereoselectivity", *Bulletin of the Chem. Soc. of Japan* 47(7):1698 (1974).

CATIONIC RHODIUM BIS(DIOXAPHOSPHORUS HETEROCYCLE) COMPLEXES AND THEIR USE IN THE BRANCHED PRODUCT REGIOSELECTIVE HYDROFORMYLATION OF OLEFINS

Cross-Reference to Related Applications

This is a division of application Ser. No. 07/587,186, filed Sep. 24, 1990, U.S. Pat. No. 5,179,055.

FIELD OF THE INVENTION

The present invention pertains to novel cationic rhodium complexes of bis(1,3,2-dioxaphosphorus heterocycle) ligands for use in maximizing the production of branched aldehydes in the hydroformylation of olefins. Selectivity for the branched aldehyde isomer is important in the synthesis of many pharmaceutical agents. The particular regioselective hydroformylation reaction catalyzed by the use of cationic rhodium complexes of the present invention is selective for the α-substituted aryl aldehydes in a maximal way and results in the formation of a branched isomer that is useful for the synthesis of pharmaceuticals such as ibuprofen.

BACKGROUND OF THE INVENTION

In general, the hydroformylation reaction involves the addition of carbon monoxide and hydrogen to an olefin containing a substituent group. In this reaction, two isomers are formed in which one is linear, A, and the other is branched, B.

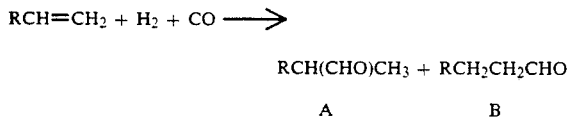

$$RCH=CH_2 + H_2 + CO \longrightarrow$$

$$\underset{A}{RCH(CHO)CH_3} + \underset{B}{RCH_2CH_2CHO}$$

The history of the utility of hydroformylation reactions has focused principally on the preparation of linear products for subsequent use in making surfactants and detergents; however, the branched product is also very important for use in preparing speciality chemicals or pharmaceutical chemicals.

Selectivity for the branched or the linear isomer is important in producing a single, pure product, and selectivity can be obtained by manipulating the structure of a catalyst for the reaction, which is typically based on rhodium or cobalt.

Through the selection of a single, pure product, a better and more efficient route to the production of α-aryl aldehydes is obtained, and these aldehydes are precursors to α-aryl carboxylic acids, such as those forming the base for ibuprofen and naproxen.

Regioselective rhodium catalyzed hydroformylation, as reported by Amer, I., et al, *J. Amer. Chem. Soc.*, 112, 3675 (1990), involves as catalyst a simple zwitterionic π-arene complex of Rh(1,5-cyclooctadiene)+ and $BF_4^-$. This process is conceptually simple and the selectively, which is typically up to 98% branched, is very good; however, the range of substrates reported therein do not include β-substituents (as in the case of methyl styrene).

Drent, E., UK patent appl. GB 2217318, discloses the use of a formula based on aryl phosphite and neutral Rh(I) that provides modest selectivity when the olefin containing substituent is vinyl acetate.

Neibecker, B. et al, *J. Org. Chem.*, 54, 5208 (1989), discloses the use of a system based on a specific phosphine ligand that gives only 80–95% selectivity for the branched isomer.

In the regioselective catalyzed system of Brown, J.M. et al, *Tetrahedron*, 42, 5105 (1988), reliance is based upon a large, very flexible disaccharide backbone; however, the backbone ligand is not easy to make and it is useful for only a limited range of substrates.

A survey of reactions of simple rhodium carbonyl catalysts that, at certain high pressures and temperatures, is very effective, i.e., up to a 98:2 ratio, is reported in Lazzaroni, R. et al, *J. Mol. Cat.*, 50, 1 (1969).

Other literature and patent references pertaining to selective hydroformylation are as follows: Agency of Industrial Sciences and Technology, JP 48099131; Tanaka, M. et al, *Bull. Chem. Soc. Jpn.*, 47, 1698 (1974); Fujimoto, M. et al., JP 52062233; Pittman, C.U. Jr. et al., *J. Org. Chem.*, et al, 43, 4928 (1978); Lai, V., et al, *J. Mol. Catal.* 4, 401 (1978); Takeda, et al, JP 54024843; Tinker, Harold B., et al., U.S. Pat. No. 4,268,688; and Hayashi, T. et al, *J. Mol. Catal.* 13, 323 (1981).

SUMMARY OF THE INVENTION

Accordingly, it is an object of the present invention to provide new rhodium-based catalysts for hydroformylation reactions in order to select a single branched aldehyde product.

Another object of the present invention is to provide a general route to obtaining branched aldehydes in order to facilitate proficiency in the synthesis of certain pharmaceutical agents or other speciality chemicals.

A further object of the present invention is to provide catalysts consisting of cationic rhodium complexes containing a bis(dioxaphosphorus heterocycle) ligand, and applying this metal-ligand system in a hydroformylation reaction to efficiently and selectively arrive at the corresponding branched aldehydic products of the olefin.

Yet another object of the present invention is to provide appropriate reaction conditions so that said ligands or complexes will catalyze the formation of only the branched isomers derived from vinyl arenes, such as styrene or vinyl naphthalene.

A still further object of the present invention is to provide a catalyst that is effective with substrates such as β-methyl styrene in order to provide a high selectivity for the product with the formyl group next to the arene.

DETAILED DESCRIPTION OF THE PREFERRED EMBODIMENTS

It has been discovered that a novel structure of cationic rhodium complexes containing 1,3,2-dioxaphosphorus heterocyclic groups have excellent selectivity for the branched product in hydroformylation reactions. The particular cationic rhodium complexes in accordance with the present invention have the following structural formula:

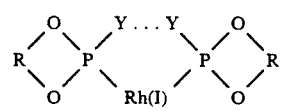

This structure includes as its major components a rhodium(I) center, two 1,3,2-dioxaphosphorus heterocyclic groups connected by their phosphorus atoms to the rhodium, and a backbone group linking the two phosphorus atoms and the rhodium atom into another ring structure. For stability the rhodium ion is also connected to a ligand structure.

The catalysts of the present invention are effective for branched regioselectivity in hydroformylation reactions because the 1,3,2-dioxaphosphorus heterocyclic groups essentially keep any catalyst substituents away from the active site at which the rhodium interacts with the reaction substrate. It is known that a crowded, or sterically hindered, catalyst will show a preference for linear regioselectivity in hydroformylation reactions. The concept in the structure of the catalyst of the present invention is to tie back the moieties connected to the phosphorus atoms so as to leave the rhodium as uncrowded as possible. This is done by means of the heterocyclic groups of the present invention.

The heterocyclic groups are shown in the above formula to be closed by an R group. The R group may be any group which includes 2 to 5 carbon atoms directly within the 1,3,2-dioxaphosphorus heterocyclic group, which carbon atoms are optionally substituted by any moiety which will not interfere with the branched product regioselectivity of the catalyst as a whole. Preferred R groups will have no substituents, but if substituents are present, the preferred substituents are those which make the oxygens of the dioxaphosphorus heterocyclic groups more electron-withdrawing as this will cause the phosphorus atoms to be electron-deficient. The smallest dioxaphosphorus heterocyclic groups are preferred as it has been shown that five-membered 1,3,2-dioxaphosphorus groups give somewhat better selectivity under identical conditions than six-membered groups. Among the groups which may be used as R include —$C_6H_4$— or —$(CR^1R^2)_x$— where x is 2-5, preferably 2 or 3, and $R^1$ and $R^2$, alike or different, may be hydrogen, lower alkyl, phenyl or a carboxylato ester, optionally substituted by any group which will not interfere with the ability of the catalyst as a whole to be branched product regioselective. On a lower alkyl group, such substituents may be trifluoro, cyano, carbonyl or any other group which makes the oxygens more electron-withdrawing. On a phenyl group, such substituents may include alkyl, alkoxy and amino, but will preferably include any group which is electron-withdrawing, e.g., halogen, nitro, etc. With respect to the carboxylato moieties, the ester may be an alkyl or aryl group, again optionally substituted by any group which will not interfere with the ability of the catalyst as a whole to be branched product regioselective.

The Y ... Y backbone group is also not critical to the catalytic activity of the catalyst as a whole. Any backbone should work well unless it somehow causes the rhodium ion to become more crowded and, thus, affect the branched product regio-selectivity of the catalyst as a whole. Examples of such backbones are —O(CH$_2$)$_y$O—, —(CH$_2$)$_y$—, —(C$_6$H$_4$)—, and —O(o—C$_6$H$_4$)O—, in which y is 2-5, preferably 2 or 3. It is also possible to use nonorganic backbones such as —O—Si—O—. Again, any backbone group which provides a chain of 2-7 atoms between the phosphorus atoms and which does not interfere with the ability of the catalyst as a whole to be branched product regioselective can be used.

Whenever the term "which does not interfere with the ability of the catalyst as a whole to be branched product regio-selective" is used throughout the present specification and claims with respect to a substituent, radical or other group, it is intended that such substituent, radical or group does not cause the hydroformylation reaction of interest to lose its selectivity for the branched aldehyde product. If the branched and linear products are approximately equal or if there is more linear product than branched then the catalyst is not considered to be branched product regioselective. As the preferred products are substantially 100% branched product regioselective, the preferred substituents, radicals or groups will not substantially affect that 100% regioselectivity and will permit at least 75% regioselectivity under pressure conditions which are commercially reasonable.

In order to determine whether a catalyst with any given substituent, radical or group falls within the definition, i.e., does not interfere with the ability of the catalyst as a whole to be branched product regioselective, one need only run routine tests, such as that detailed in Example 4 hereinbelow. Such a test does not require undue experimentation. Indeed, the determination of whether any given substituent, radical or group falls within this definition would be a matter of routine experimentation.

To be stable, the rhodium cation must be coordinated with ligands L and L' so that the stabilized catalyst will have the structure:

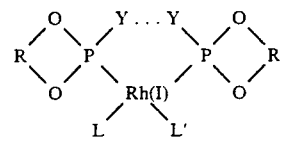

However, such ligands do not play a part in the activity of the catalyst as they are removed in situ and the rhodium ion complexes directly with the reaction substrate being catalyzed. Precatalysts, which may be stored and added to the reaction so as to form the active catalyst in situ, must have such stabilizing ligands. When the stabilizing ligands are used, the ligands may be any olefin or they may be CO groups. Alternatively, the ligands may be a coordinating solvent, such as tetrahydrofuran, acetonitrile, methylene chloride, chloroform, acetone, etc. The L and L' groups may be combined into a single diolefin, such as 1,5-cyclooctadiene (COD), norbornadiene, or 1,5-hexadiene.

The catalyst of the present invention is itself cationic. It may be prepared with any anion such as $BF_4^-$, $PF_6^-$, $ClO_4^-$, a halide, etc. The particular anion used is not part of the present invention pe se.

The catalysts of the present invention may be synthesized by first synthesizing the diphosphorus ligands and then reacting with a rhodium compound. Diphosphorus ligands containing 1,3,2-dioxaphosphorus heterocyclic groups are made by the condensation of a diol with $PCl_3$ followed by linking with a backbone diol such as 1,3-propane diol or catechol. Diols such as diisopropyltartrate, diethyltartrate and R,R-dihydrobenzoin react readily with $PCl_3$ in the presence of a base to give a chlorodioxaphosphorus heterocycle as a single stereoisomer as follows:

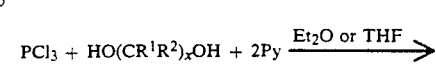

-continued

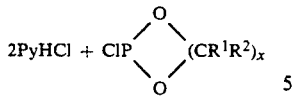

where Py is pyridine (but may be any other base), $R^1$ and $R^2$, alike or different, are trifluoro, cyano, carbonyl or any other group which makes the oxygens of the dioxaphosphorus heterocycle more electron-withdrawing, and x is 2-5. When the diol starting material is a tartrate, the diol formula has x being 2, the $R^1$ groups being hydrogen and the $R^2$ groups being —$COOR^3$ where $R^3$ is an alkyl or aryl group. When the diol starting material is dihydrobenzoin, the diol formula x being 2, $R^1$ being hydrogen and $R^2$ being phenyl. Whenever x is 2, the 1,3,2-dioxaphosphorus heterocyclic compound produced is a dioxaphospholane. Alternatively, the starting diol may be HO—(o—$C_6H_4$)—OH which is optionally substituted with one or more substituents having the same definition as $R^1$ and $R^2$.

In the case of the tartrate esters, the product is purified by distillation in vacuo while the diphenyl derivative is obtained pure after crystallization from ether. All three compounds are obtained in analytically pure form in fair to good yield (46-93%), and while these compounds are sensitive to protic solvents, they are indefinitely stable at ambient temperatures under dry nitrogen.

The formation of the bis-phosphorus ligand may be performed with any other diol in the presence of a base in accordance with the following equation:

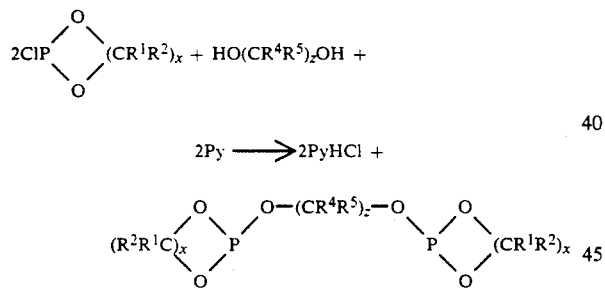

where x, $R^1$ and $R^2$ are as described above, z is 2 to 5, and $R^4$ and $R^5$ are any substituents which do not interfere with the ability of the final catalyst to be branched product regioselective. $R^4$ and $R^5$ are preferably both H and z is preferably 3. Reactions with aliphatic 1,2-diols such as ethylene glycol and pinacol are complicated by the decomposition products which appear to involve an equilibrium mixture of heterocyclic rings. Much better results are obtained with 1,3-propanediol which affords good yields (71-90%) of the desired diphosphorus products as oils. These oils can be purified to spectroscopic and analytical purity from ether. The NMR spectra of these complexes are essentially the same as their acyclic analogues (shifts in the $^{31}P$ NMR spectrum occur in a ca 0.145 ppm). They are thermally sensitive but can be stored at low temperature and handled for short periods at ambient temperatures.

Alternatively, a bis(dichlorophosphino)alkane can be reacted directly with a diol to form the bis-dioxaphosphorus heterocycle auxiliary directly, as follows:

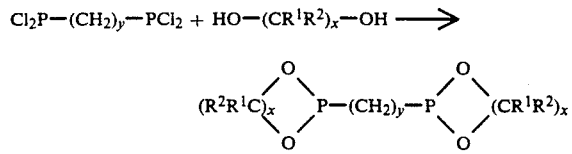

where x is 2-5, y is 2-5 and $R^1$ and $R^2$ are as defined above.

Once the bis(1,3,2-dioxaphosphorus heterocycle) compounds are obtained they can readily form cationic rhodium precatalysts by reaction with a Rh(I) rhodium compound such as $Rh(I)^+L_n^-$ or $Rh(I)^+L_nX^-$. In the first instance L is an anionic coordinating ligand such as $CO_2Cl$ or a coordinating solvent such as tetrahydrofuran, acetonitrile, methylene chloride, chloroform, acetone, etc. In the second instance L is a neutral ligand such as an olefin or carbon monoxide. The neutral ligand may be a cyclic group such as 1,5-cyclooctadiene (1,5-COD). n may be any number above 0 as long as the ligand is complexed with the rhodium cation. The anion $X^-$ may be any non-coordinating anion such as $BF_4^-$, $PF_6^-$, $ClO_4^-$, a halide, etc. A preferred rhodium compound for making a stable rhodium precatalyst is bis(1,5-cyclooctadiene) rhodium tetrafluoroborate. This compound gives a good yield of analytically and spectroscopically pure complex salts.

Example 1 - Synthesis of 2-chloro-1,3,2-dioxachosoholanes

Phosphorus trichloride (3.2 g. 23 mmol) was dissolved in 60 ml of tetrahydrofuran (THF). A solution of R,R-dihydrobenzoin (5.00 g. 23.4 mmol) and anhydrous pyridine (4 ml, 51 mmol) in 60 ml THF was added dropwise while the reaction flask was cooled in an ice water bath. The resulting white suspension was stirred overnight at room temperature and filtered. The product was isolated as spectroscopically pure colorless crystals (5.1 g 80%) after crystallization from diethyl ether at −78° C.

The tartrate ester derivatives were synthesized by addition of the $PCl_3$ solution to the diol/pyridine solution, and superior yields were obtained if the reaction was left to stir for several days. The clear, colorless filtrate was concentrated in vacuo and the crude product purified by vacuum (ca. $10^{-3}$ Torr) distillation. Typical yields of purified products: from diethyltartrate were 93% (b p., 93°-95° C., 10-3 Torr); and from diisopropyltartrate: 46% (b.p., 108°-110° C.).

Example 2 - Synthesis of propane-bridged bis(dioxaphospholane)s

The chlorodioxaphospholane (3.00 g. 11 mmol) was dissolved in 20 ml THF. This solution was immersed in ice water and, with stirring, a solution of 1,3-propanediol (0.41 g. 5.4 nmol) and anhydrous pyridine (1 ml. 0.013 mol) in 15 ml THF was added dropwise over a period of 30 minutes. The mixture (which turns into a white suspension), was stirred for an additional 3 hours and then filtered. The solvent was removed in vacuo and the product purified by extraction with ether and then filtered and concentrated to give a colorless, spectroscopically pure oil (2.8 g 90%). Typical yields of purified products from diethyltartrate are 77%; and from diisopropyltartrate: 71%.

Example 3 - Synthesis of (1,5-cyclooctadiene)bis(dioxaphospholane) rhodium(I) tetrafluoroborates The bis(dioxaphospholane) (0.69 g, 0.12 mmol) was dissolved in 5 ml methylene chloride and added, via cannula, to a solution of bis(1,5-cyclooctadiene)rhodium(I)tetrafluoroborate (0.50 g, 1.23 mmol) in 10 ml $CH_2Cl_2$. The bright orange solution was concentrated in vacuo and the residue was extracted with chloroform. The product was precipitated from solution by the addition of $Et_2O$ (0.88 g 83%). Typical yields of purified products from diethyltartrate are 54%; and from diisopropyltartrate: 55%.

Example 4 - Hydroformylation reactions

A hydroformylation reaction was performed by loading substrate and catalyst into a bomb in an inert atmosphere and then pressurizing to the appropriate initial pressure with 1:1 $CO:H_2$. The reaction was then heated externally in an oil bath at 70° C. and then stopped after 24 hours, and the vessel was then vented and opened to the air. Reaction products were determined by an examination of the reaction mixture by $^1H$ NMR after removal of most of the solvent by a stream of nitrogen or in a vacuum. Quantitative amounts of the linear and branched isomer were determined by comparison of the integrals of the signal for the linear isomer with the nearest $^{13}C$ satellite of the branched isomer. Where complete regioselectivity is obtained, as in equation 2, this means that the $^{13}C$ satellites of the branched isomer are clearly visible while a signal for the linear isomer is not. This corresponds to at least a 200:1 ratio of branched to linear isomer.

In this example the substrate was styrene and the catalyst was:

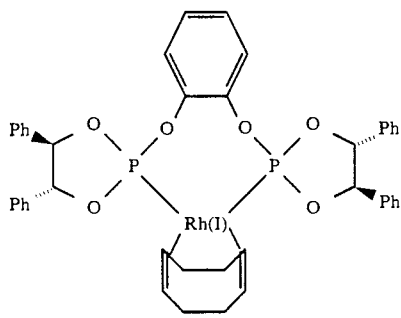

When the reaction was performed at 250 psi, the product contained 85% of the branched product: phCH(CHO)CH₃ and 15% of the linear product: $PhCH_2CH_2CHO$. When repeated at 700 psi, complete selectivity for the isoaldehyde was obtained.

Example 5

The hydroformylation reaction of Example 4 was repeated using vinyl naphthalene as the substrate. At 700 psi the selectivity was 98% for the branched aldehydic product.

Example 6

The hydroformylation reaction of Example 4 was repeated using vinyl acetate as the substrate. At 700 psi the selectivity was 100% for the branched aldehydic product.

Example 7

The hydroformylation reaction of Example 4 was repeated using β-methyl styrene as the substrate. At 1450 psi 94% selectivity for the α-aldehyde is obtained. Thus, even with disubstituted olefins selectivity for the α-aldehyde product, while not 100%, is far superior to any prior art literature reports.

In principle, the versatility of the formyl group created in the hydroformylation indicates that the catalyst of the present invention can be useful in countless applications. However, two problems can be easily resolved through the use of the catalyst of the present invention under the conditions described. Namely, the simple production of α-aryl aldehyde and the synthesis of chiral precursors for heterocycle synthesis.

The α-aryl aldehydes are important precursors to α-aryl carboxylic acids that are the basis for a family of important biologically active agents sold over-the-counter, as, for example, the drug ibuprofen and the proprietary drug naproxen. Hydroformylation of an aryl olefin is an extremely attractive route to the aldehyde, which can be conveniently oxidized to the acid, and the catalyst of the present invention can be a method of choice for α-aryl aldehyde synthesis because the selectivity is so much higher than that in other systems.

In the synthesis of chiral precursors for heterocycle synthesis, aldehydes are also effective reagents relevant to pharmaceutical development, especially when the α-carbon is branched, and the scope of the applications envisioned can, for example, be described in reference to the following two recent reports:

1) Danishefsky and coworkers have developed the Lewis-acid catalyzed condensation (LACDAC) of activated dienes and aldehydes as a route to furan synthesis and, by elaboration of the furan, to a myriad of natural products (cf. Danishefsky, S. *Chemtracts*, 1989, 2, 273). The reaction is capable of generating new stereocenters with excellent selectivity if the aldehyde is branched at the α-position; and 2) A second application relies on methodology developed by Trost (cf. Trost, B.M. *Angew. Chem., Int. Ed., Engl.*, 25, 1, (1988)) and Tsuju (cf. Shimuzu, I., et al *Tetrahed. Lett.*, 25, 5183 (1984)) for palladium catalyzed formation of five-membered rings. Trost has shown that, with aldehydes, this constitutes a general route to substituted methylene furans (cf. Trost, B.M. et al., *J. Amer. Chem. Soc.*, 112, 408 (1990)) Trost, B.M. et al., *J. Amer. Chem. Soc.*, 11, 5902 (1989)); Trost, B.M. et al., *J. Amer. Chem. Soc.*, 107, 8277 (1985)).

As to the item 1) above, the method of the present invention may be used to greatly increase the number and complexity of substrates suitable for the Lewis-acid catalyzed condensation of activated dienes and aldehydes. In connection with item 2) above, the method of the present invention can provide chiral aldehydes that induce excellent stereo-selectivity in the reaction, and the products formed can be elaborated into natural products and prodrugs.

While the invention has been described with specific reference to the use of the cationic rhodium bis 1,3,2-dioxaphosphorus complexes for hydroformylation of olefins to branched aldehydes, it is to be understood that said examples are for purposes of illustration only and are not to be construed as limitations upon either the use of said catalysts or the processes specifically described using said catalysts, and that the catalyst complexes as well as the processes of using the same can be applicable to any rhodium catalyzed hydroformylation reaction where regioselectivity is sought for the branched aldehydic product and in the synthesis of chiral precursors for heterocycle synthesis, without departing from the spirit and scope of the invention, which is defined in the appended claims.

What is claimed is:

1. In the method for the hydroformylation of olefins in which hydrogen and carbon monoxide are reacted with an olefin to yield two isomeric forms of an aldehyde, at least one of which is branched, said reaction taking place in the presence of a catalyst, the improvement whereby the reaction is regioselective for a branched aldehyde, wherein:

said catalyst has the formula:

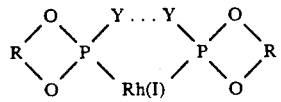

wherein R is any group which includes 2-5 carbon atoms directly within the 1,3,2-dioxaphsophorus heterocyclic group and which does not interfere with the branched aldehyde regioselectivity of the catalyst as a whole, and Y . . . Y is any chain of 2-5 atoms which does not interfere with the ability of the catalyst as a whole to be branched aldehyde regioselective, and wherein the reaction takes place at a temperature and pressure sufficient to yield an aldehyde reaction product in which a branched aldehyde predominates.

2. A method in accordance with claim 1, wherein R is —$(CR^1R^2)_x$— in which x is 2-5, $R^1$ and $R^2$, alike or different, are hydrogen or any group which will not interfere with the ability of the catalyst as a whole to be branched aldehyde regioselective, or a phenyl group connected at ortho carbon atoms to the oxygen atoms of the dioxaphosphorus heterocycle, said phenyl group being unsubstituted or substituted by a substituent which will not interfere with the ability of the catalyst as a whole to be branched aldehyde regioselective.

3. A method in accordance with claim 2, wherein x is 2.

4. A method in accordance with claim 2, wherein $R^1$ and $R^2$, alike or different, are hydrogen, lower alkyl, phenyl or a carboxylato ester, wherein the alkyl, phenyl or carboxylato ester groups are unsubstituted or substituted by any group which will not interfere with the ability of the catalyst as a whole to be branched aldehyde regioselective.

5. A method in accordance with claim 4, wherein $R^1$ and $R^2$, alike or different, are hydrogen or a carboxylato ester wherein the ester is an alkyl or aryl group.

6. A method in accordance with claim 1, wherein said Y . . . Y group is —$O(CH_2)_yO$—, —$(CH_2)_y$—, —$(C_6H_4)$—, —$O(o—C_6H_4)O$— or —$O—Si—O$—, in which y is 2-5.

7. A method in accordance with claim 1 wherein said olefin is selected from the group consisting of vinyl acetate, styrene, vinylnaphthalene and β-methyl styrene.

8. A method in accordance with claim 1, wherein R is —$(CR^1R^2)_x$— in which x is 2-5, $R^1$ and $R^2$, alike or different, are hydrogen or any group which will not interfere with the ability of the catalyst as a whole to be branched aldehyde regioselective, or a phenyl group connected at ortho carbon atoms to the oxygen atoms of the dioxaphosphorus heterocycle, said phenyl group being unsubstituted or substituted by a substituent which will not interfere with the ability of the catalyst as a whole to be branched aldehyde regioselective.

9. A method in accordance with claim 8, wherein x is 2.

10. A method in accordance with claim 8, wherein $R^1$ and $R^2$, alike or different, are hydrogen, lower alkyl, phenyl or a carboxylato ester, wherein the alkyl, phenyl or carboxylato ester groups are unsubstituted or substituted by any group which will not interfere with the ability of the catalyst as a whole to be branched aldehyde regioselective.

11. A method in accordance with claim 10, wherein $R^1$ and $R^2$, alike or different, are hydrogen or a carboxylato ester wherein the ester is an alkyl or aryl group.

12. A method in accordance with claim 11, wherein said Y . . . Y group is —$O(CH_2)_yO$—, —$(CH_2)_y$—, —$(C_6H_4)$—, —$O(o—C_6H_4)O$— or —$O—Si—O$—, in which y is 2-5.

13. A method in accordance with claim 11, wherein L and L' are an olefin, CO, a coordinating solvent, or both L groups combine into a diolefin, and said anion is also present.

14. A method in accordance with claim 11, wherein said anion is $BF_4^-$, $PF_6^-$, $ClO_4^-$ or a halide.

15. In the method for the hydroformylation of olefins in which hydrogen and carbon monoxide are reacted with an olefin to yield two isomeric forms of an aldehyde, at least one of which is branched, said reaction taking place in the presence of a catalyst, the improvement whereby the reaction is regioselective for a branched aldehyde, wherein:

said catalyst has the formula:

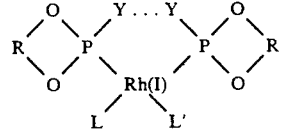

wherein R is any group which includes 2-5 carbon atoms directly within the 1,3,2-dioxaphosphorus heterocyclic group and which does not interfere with the branched aldehyde regioselectivity of the catalyst as a whole, Y . . . Y is any chain of 2-5 atoms which does not interfere with the ability of the catalyst as a whole to be branched aldehyde regioselective, and L and L' are any ligand which complexes with the rhodium(I) atom in order to stabilize the molecule prior to use but which leaves the molecule in situ, and wherein L and L' are both neutral, an anion is also present, and wherein the reaction takes place at a temperature and pressure sufficient to yield an aldehyde reaction product in which a branched aldehyde predominates.

16. A method in accordance with claim 1, wherein said olefin is an aromatic olefin.

17. A method in accordance with claim 16, wherein said olefin is an aromatic olefin with a β-substituent.

18. A method in accordance with claim 1, wherein said olefin has the terminating moiety —CH=$CH_2$ and the two isomeric forms of aldehyde which are produced are a linear form and a branched form, and wherein the reaction is regioselective for the branched aldehyde.

19. A method in accordance with claim 15, wherein said olefin is an aromatic olefin.

20. A method in accordance with claim 19, wherein said olefin is an aromatic olefin with a β-substituent.

21. A method in accordance with claim 19, wherein said olefin is selected from the group consisting of styrene, vinyl acetate, vinylnaphthalene and β-methyl styrene.

22. A method in accordance with claim 15, wherein said olefin has the terminating moiety —CH=CH$_2$ and the two isomeric forms of aldehyde which are produced are a linear form and a branched form, and wherein the reaction is regioselective for the branched aldehyde.

* * * * *